United States Patent
Hadlock et al.

(10) Patent No.: US 6,214,021 B1
(45) Date of Patent: *Apr. 10, 2001

(54) MULTI-LUMEN POLYMERIC GUIDANCE CHANNEL AND METHOD OF MANUFACTURING A POLYMERIC PROSTHESIS

(75) Inventors: Theresa Anne Hadlock, Arlington; Cathryn Sundback, Harvard, both of MA (US)

(73) Assignee: Children's Medical Center Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/145,727

(22) Filed: Sep. 1, 1998

Related U.S. Application Data

(63) Continuation-in-part of application No. 08/921,908, filed on Sep. 2, 1997, now Pat. No. 5,925,053.

(51) Int. Cl.⁷ .................................................... A61B 17/08
(52) U.S. Cl. ............................................. 606/152; 264/29
(58) Field of Search .................................. 606/152, 153, 606/154, 155, 156

(56) References Cited

U.S. PATENT DOCUMENTS

| | | | |
|---|---|---|---|
| 3,812,224 | * 5/1974 | Smith et al. | 264/28 |
| 3,933,957 | * 1/1976 | White | 264/29 |
| 4,060,081 | 11/1977 | Yannas et al. | 128/156 |
| 4,418,691 | 12/1983 | Yannas et al. | 128/156 |
| 4,458,678 | 7/1984 | Yannas et al. | 128/155 |
| 4,505,266 | 3/1985 | Yannas et al. | 128/1 R |
| 4,759,764 | 7/1988 | Fawcett et al. | 623/12 |
| 4,778,467 | 10/1988 | Stensaas et al. | 623/12 |
| 4,806,621 | 2/1989 | Kohn et al. | 528/211 |
| 4,878,913 | 11/1989 | Aebischer et al. | 623/12 |
| 4,947,840 | 8/1990 | Yannas et al. | 128/156 |
| 4,955,893 | 9/1990 | Yannas et al. | 606/154 |
| 5,011,486 | 4/1991 | Aebischer et al. | 606/152 |
| 5,024,671 | 6/1991 | Tu et al. | 623/1 |
| 5,026,381 | 6/1991 | Li | 606/152 |
| 5,030,225 | 7/1991 | Aebischer et al. | 606/152 |
| 5,047,181 | 9/1991 | Occhionero et al. | 264/28 |
| 5,092,871 | 3/1992 | Aebischer et al. | 606/152 |
| 5,202,120 | 4/1993 | Silver et al. | 424/93 |
| 5,358,475 | 10/1994 | Mares et al. | 623/66 |
| 5,370,681 | 12/1994 | Herweck et al. | 623/1 |
| 5,399,665 | 3/1995 | Barrera et al. | 528/354 |
| 5,502,092 | * 3/1996 | Barrows et al. | 521/64 |
| 5,514,378 | 5/1996 | Mikos et al. | 424/425 |
| 5,654,381 | 8/1997 | Hrkach et al. | 525/450 |
| 5,656,605 | 8/1997 | Hansson et al. | 514/21 |

FOREIGN PATENT DOCUMENTS

| | | |
|---|---|---|
| 8806871 | 9/1988 | (WO) . |
| 9005490 | 5/1990 | (WO) . |

* cited by examiner

*Primary Examiner*—Gary Jackson
*Assistant Examiner*—Vy Q. Bui
(74) *Attorney, Agent, or Firm*—Thomas J. Engellenner; Nutter, McClennen & Fish, LLP

(57) ABSTRACT

A guidance channel or conduit for promoting nerve regeneration includes a body constructed of a biocompatible polymeric material and having a first end for connection to a proximal stump of a severed nerve and a second end for connection to a distal stump of the severed nerve. The body includes a plurality of internal lumens extending between the first and second end to facilitate rejoining of the proximal and distal stumps of the severed nerve by providing increased surface area for Schwann cell adherence. A method for promoting nerve regeneration using a multi-lumen nerve guidance channel is also disclosed.

14 Claims, 8 Drawing Sheets

MULTI-LUMEN POLYMERIC GUIDANCE CHANNEL AND METHOD OF MANUFACTURING A POLYMERIC PROSTHESIS

REFERENCE TO RELATED APPLICATIONS

This application is a continuation-in-part of U.S. patent application No. Ser. 08/921,908, filed Sep. 2, 1997 U.S. Pat. No. 5,925,053, incorporated herein by reference.

BACKGROUND OF THE INVENTION

The present invention relates generally to repairing injured nerves. More particularly, the invention relates to a guidance channel or conduit, as well as a method, for promoting nerve regeneration.

Various prostheses and nerve grafts have been proposed for repairing severed nerves. Typical prostheses include synthetic tubular bodies having a single lumen through which nerve regeneration is intended to occur. These nerve guidance devices are surgically inserted into the gap between the proximal and distal nerve stumps in an effort to promote nerve growth.

Conventional nerve guidance channels are often unsuccessful. When a nerve is injured, Schwann cells stimulate the growth of the regenerating nerve fibers by dividing and producing the trophic substances responsible for nerve growth. Accordingly, Schwann cells appear to play an important role in the regeneration of nerve tissue in an injured or severed nerve. One cause of failure in conventional nerve prostheses and grafts appears to be due to a lack of support for a sufficient number of Schwann cells to ensure successful nerve regeneration.

Accordingly, there is a need for an improved nerve prosthesis for promoting increased and reliable nerve regeneration between the distal and proximal stumps of a severed nerve.

It is, therefore, an object of the present invention to provide an effective nerve guidance channel for promoting nerve regeneration.

It is another object of the present invention to provide a nerve guidance channel which provides increased surface area for Schwann cell adherence.

It is also an object of the present invention to provide a more flexible and preferably biodegradable prosthesis that does not cause discomfort or require surgical removal.

It is a further object of the present invention to provide a nerve guidance channel or conduit that permits increased control over the direction of growth of regenerating nerve fibers.

SUMMARY OF THE INVENTION

The present invention is directed to a guidance channel or conduit and a method for promoting nerve regeneration. The guidance channel includes a body constructed of a biocompatible polymeric material and having a first end for connection to a proximal stump of a severed nerve and a second end for connection to a distal stump of the severed nerve. The body includes a plurality of internal lumens extending between the first and second end to facilitate rejoining of the proximal and distal stumps of the severed nerve by providing increased surface area for Schwann cell adherence.

In a preferred embodiment, the guidance channel is constructed of a bioresorbable or biodegradable material, such as poly-L-lactic acids, poly-lactic-coglycolic acid polymers, poly-glycolic acid polymers, and polycaprolactones. The guidance channel can include between 5 and 5000 lumens. The inner diameter of each lumen is can be between approximately 2 and 500 microns.

In accordance with a further aspect of the present invention, Schwann cells are incorporated within the lumens of the nerve guidance channel body. The Schwann cells can adhere to the interior surfaces of the lumens.

In accordance with another aspect of the present invention, the body of the nerve guidance channel is constructed of a porous membrane structure which contains a plurality of pores for permitting fluids and nutrients to pass through the body of the guidance channel to reach the internal lumens. In this manner, Schwann cells and regenerative nerve tissue within the internal lumens are able to receive nutrients and oxygen during nerve regeneration. It is preferable for the pores to be sized to inhibit the growth of regenerative nerve tissue through the pores.

The method of the present invention provides for promoting nerve regeneration between the severed stumps of a nerve. The method includes the steps of providing a guidance channel constructed of a polymeric material and having a plurality of internal lumens extending between the first end and the second end of the guidance channel, connecting the proximal stump of the nerve to the first end of the guidance channel, and connecting the distal stump of the nerve to the second end of the guidance channel such that nerve regeneration occurs within the plurality of lumens of the guidance channel between the severed stumps of the nerves.

In accordance with a further aspect of the present invention, the method includes the step of lining the lumens of the plurality of lumens with Schwann cells.

A method of manufacturing a multi-lumen nerve guidance channel in accordance with present invention includes the steps of preparing a polymer solution comprising a polymer and a solvent, injecting the polymer solution into a mold to form the body of the nerve guidance channel, the mold including a plurality of wires for forming a plurality of internal lumens within the body, solidifying the polymer solution by freezing the body, and drying the body by sublimation to form a plurality pores within the body.

In accordance with another aspect of the present invention, the manufacturing method includes the step of adjusting the concentration of the solvent within the polymer solution to control the size and number of pores formed within the body.

A method for manufacturing a polymeric prosthesis for use in tissue engineering and regeneration in accordance with present invention includes the steps of preparing a polymer solution by dissolving a polymer in a solvent, injecting the polymer solution into the mold cavity, solidifying the polymer solution by freezing the polymer solution in the mold to form the polymeric prosthesis, and drying the polymeric prosthesis by sublimation. The injection molding process of the present invention permits the fabrication of biocompatable and biodegradable polymer prosthesis with controlled, precise dimensions, high tolerances, and controlled porosity. Polymeric prostheses manufactured according to the injection molding method of the present invention can be used in the tissue engineering and regeneration of a wide range of tissue types, including structural tissues, such as bone, muscle, or cartilage, and specialized tissues such as organ tissue, including brain and liver tissue, and breast tissue.

BRIEF DESCRIPTION OF THE DRAWINGS

These and other features and advantages of the present invention will be more fully understood by reference to the following detailed description in conjunction with the attached drawings in which like reference numerals refer to like elements and in which.

DETAILED DESCRIPTION

Figure 1:
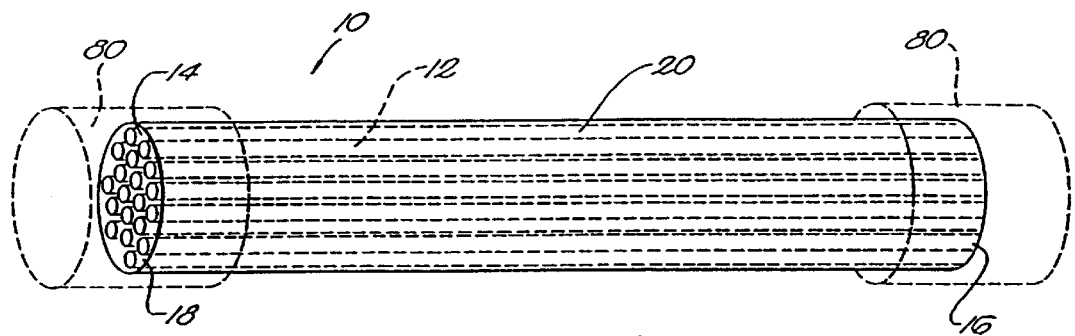
FIG. 1 is a perspective views of the nerve guidance channel of the present invention.
Figure 2:
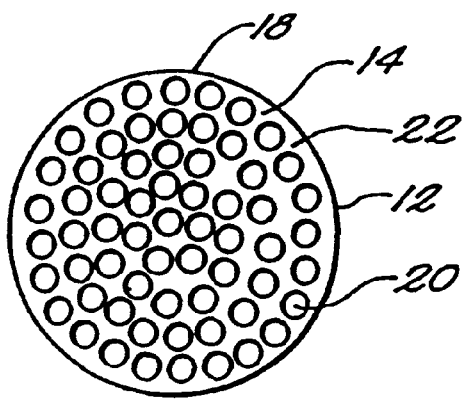
FIG. 2 is a front elevational view of the nerve guidance channel of FIG. 1, showing an end of the nerve guidance channel.

A nerve guidance channel 10 for promoting nerve regeneration is shown in FIGS. 1 and 2. The nerve guidance channel 10 includes a body 12 having a first end 14 and a second end 16.

The body 12 includes an outer shell 18 and plurality of internal lumens 20. Each of the internal lumens 20 extends continuously through the length of the body 12 to open at both the first and second ends 14, 16. The internal lumens 20 provide an internal architecture of continuous, longitudinally aligned hollow channels to promote nerve regeneration. The guidance channel can include between 5 and 500 lumens. The number of lumens is dependent on the fascicularity of the nerve as well as the number of myelinated axons expected to regenerate. The inner diameter of each lumen can be between approximately 2–500 microns.

The walls of the internal lumens 20 can be seeded with Schwann cells, which play an important role in the regeneration of nerve tissue. The Schwann cells can be introduced to the internal lumens 20 through a dynamic seeding system which includes a closed loop system maintained within an environmentally controlled incubator. The incubator maintains the fluids within the loop at physiological temperature. The loop tubing is permeable to atmospheric gases so that oxygen and carbon dioxide can diffuse into and out of the loop fluid to provide oxygen, remove waste, and maintain physiological pH. A laminin solution or other extra-cellular matrix protein solution is first pumped through the lumens 20. The laminin solution coats the surfaces of the internal lumens 20 to improve Schwann cell adherence to the lumens. A cell suspension containing Schwann cells is then pumped through the internal lumens 20 to effect seeding of the internal lumens.

Alternatively, the walls of the internal lumens 20 can be pre-wet or coated with a laminin solution by exposing the body 12 to the laminin solution under vacuum conditions. For example, the body 12 can be placed within the laminin solution and then be subjected to pressure cycling in which the pressure on the body 12 is cycled from a low pressure, preferably vacuum pressure, i.e. pressure low enough to make water boil at room temperature, or lower than vacuum pressure, to a high pressure, preferably atmospheric pressure, to evacuate substantially all air or other gases from the body 12. The body 12 can remain in the laminin solution under vacuum conditions, preferably for several hours, to pre-wet the body 12 with the laminin solution.

An alternate method of seeding the walls of the internal lumens 20 of the body 12 includes filling each of the internal lumens 20 with a high concentration Schwann cell suspension. The first and second ends 14, 16 of the body 12 can then plugged to seal the Schwann cell suspension in the internal lumens 20. The body 12 can then be rolled, for example on a roller mill, to induce uniform coating of the walls of the internal lumens 20.

Other nerve regeneration promoting substances such as fibronectin, nerve growth factor, and extracts of central nervous tissue can be provided within the internal lumens 20 or within the polymer walls of the lumens to further promote nerve regeneration.

The internal architecture of the plurality of lumens 20 within the body 12 provides increased surface area for Schwann cell adherence. This architecture thus allows the nerve guidance channel of the present invention to contain significantly more Schwann cells than conventional single lumen guidance channels. The greater number of Schwann cells within the guidance channel can provide for increased nerve regeneration.

Figure 1A:
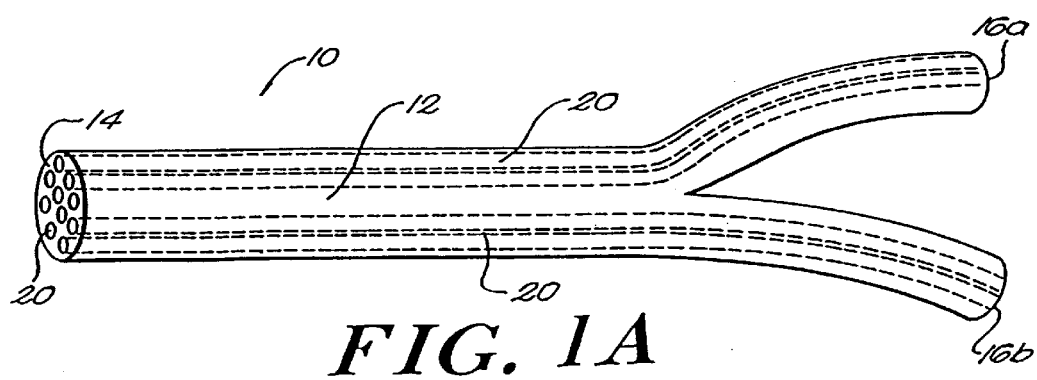
FIG. 1A is a perspective view of an alternative embodiment of the nerve guidance channel of the present invention.

In addition, the internal architecture of lumens 20 can provide increased control over the direction of growth of different groups of regenerating nerve fibers. A single nerve can contain thousands of nerve fibers or axons. By using multiple internal lumens, each axon or a group of axons can be guided during the regenerative process through an individual internal lumen or group of lumens. Thus branching architecture can be created if desired. For example, in the simple model of a bifurcating nerve, two distinct groups of internal lumens can be provided within the body of the nerve guidance channel, as shown in FIG. 1A. At the first (proximal) end 14 of the guidance channel the two distinct groups of lumens are adjacent one another to provide a single proximal end for connection with the proximal nerve stump. At the second (distal) end 16 of the guidance channel the two distinct groups of lumens separate, so that two distinct distal ends 16a, 16b of the guidance channel are provided. Each of these ends connect to a separate branch of the distal nerve stump.

The body 12 can be constructed of a resilient, porous biocompatible material that permits fluids and nutrients to penetrate the outer surface 18 and bulk 22 of the body 12 to reach the internal lumens 20. In this manner, nutrients and oxygen are able to reach the Schwann cells and regenerative tissue present in the internal lumens. It is preferable for the pores to be sized to inhibit the growth of regenerative nerve fibers through the pores instead of along the internal lumens.

Suitable biocompatible materials for the guidance channel of the present invention include synthetic polyesters that can be arranged to form a porous structure. It is preferable for the body 12 of the nerve guidance channel to be constructed of a bioresorbable or biodegradable material so that is unnecessary to surgically remove the nerve guidance channel once nerve regeneration is complete. One skilled in the art will recognize that the rate of degradation of the material within the body can be controlled by adjusting the composition of the bioresorbable/biodegradable material. The terms "biodegradable material" and "bioresorbable material" as used herein refer to materials that are capable of being readily decomposed within the subject's body by biological means, without requiring surgical removal or further treatment. For example, in certain applications, the biodegradable or bioresorbable materials useful in the present invention can be formulated to decompose within the subject's body over a period of several months, e.g. losing at least half of their original mass within six months following implantation. Example of suitable bioresorbable or biodegradable materials include poly-L-lactic (PLA) acid polymers, poly-lactic-coglycolic (PLGA) acid polymers, poly-gycolic (PGA) acid polymers, and polycaprolactones. Further suitable biodegradable or bioresorbable materials are described in U.S. Pat. Nos. 4,806,621; 5,399,665 and 5,654,381, each of which is incorporated herein by reference.

Figure 3:
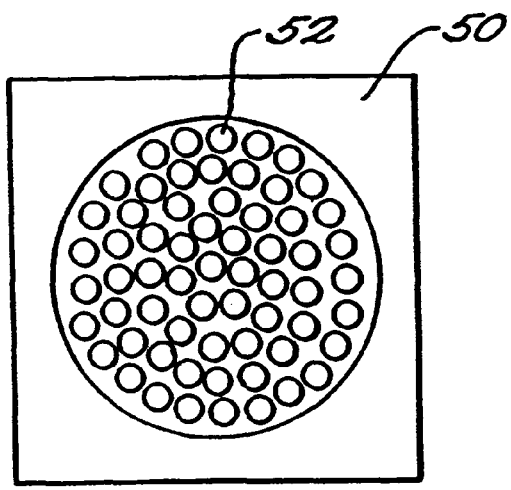
FIG. 3 is a front elevational view of a die suitable for use in constructing the nerve guidance channel of the present invention.

The nerve guidance channel of the present invention can be formed through an extrusion process in which a polymer is extruded through a die, as described in U.S. Pat. No. 5,370,681, incorporated herein by reference. The die 50 can include a plurality finger-like projections 52 for forming the internal lumens 20, as shown in FIG. 3A. Each finger-like projection 52 corresponds to an internal lumen. By varyino the number of projections in the die, the number of internal lumens 20 within the body 12 can be adjusted.

Once the polymer is extruded, it is stretched and/or expanded and then sintered while being held in the stretched and/or expanded state. Stretching refers to elongation of formed polymer while expansion refers to enlargement of the formed polymer perpendicularly to its longitudinal axis. The rate of stretching and the stretch ratio, as well as the temperature, can be adjusted to produce the desired porosity of the material.

Typically, the body 12 is tubular or cylindrical in construction having a circular cross-section as shown in FIG. 2. It can however be adapted to other profiles for different applications. For example, the body can be extruded in a D-shaped with a flat or flattened surface.

An alternate method of manufacturing a polymeric prosthesis for use in tissue engineering, such as a multi-lumen nerve guidance channel, in accordance with present invention includes injection molding a polymer solution in a mold. The term "prosthesis" used herein generally refers to any artificial replacement or substitute for a body part and is intended to include, for example, organs, vascular and arterial grafts, and bone, muscle, and cartilage replacements, as well as nerve guidance channels. The injection molding process of the present invention will be described with reference to FIG. 5.

Figure 5:
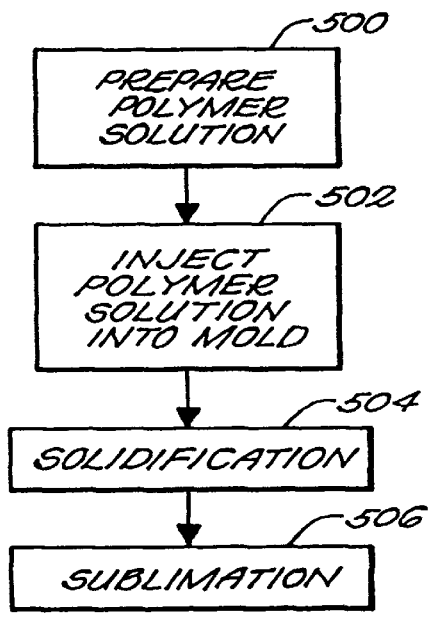
FIG. 5 is a generalized flow-chart of a method of manufacturing a polymeric prosthesis according to the teachings of the present invention.

A pourable polymer solution containing a single or combination of biodegradable and/or biocompatible polymers, such as polylactic acid (PLA), polyglycolic acid (PGA) or polylactide co-glycolide (PLGA), is prepared by dissolving the polymer in an appropriate solvent, block 500 of FIG. 5.

The solvent can be any solvent in which the polymer is soluble and the solution is pourable at the desired concentration. Pourable, as used herein, refers to flow in a constant stream under a gravity head. The desired concentration is approximately equal to the desired prosthesis porosity, as described below. Suitable solvents for PLGA include aromatics, such as benzene and toluene, chlorinated hydrocarbons, such as methylene chloride and chloroform, and acetic acid. Acetic acid is a preferred solvent because the solidification and sublimation steps described below can be conducted at easily obtained temperature and pressure conditions and because acetic acid presents lower health and safety risks than other suitable solvents.

The concentration of the polymer in the polymer solution is limited to a certain range for each polymer/solvent combination. For example, the lower limit of the polymer concentration is defined by the concentration of polymer at which the resultant polymer prosthesis has the minimum structural integrity for its intended purpose. The upper limit for polymer concentration is the maximum concentration at which the polymer solution remains pourable.

After the polymer solution is prepared, the solution is injected into a closed mold under low pressure, block 502 of FIG. 5. Solidification of the polymer solution preferably occurs by freezing, block 504. The rate of solidification, in part, defines the internal porous microstructure, including the size and number of pores. The porous microstructure has at least an approximately 70% pore volume. Preferably, the pore volume is approximately 80%. Even more preferably, the pore volume is approximately 90%. The rate of solidification can be controlled by the varying the mold temperature and the polymer solution injection temperature, and is also dependent on the geometry of the desired prosthesis.

Preferably, the mold is chilled significantly below the freezing temperature of the polymer solution to increase the rate of solidification. For example, in applications in which acetic acid, having a freezing temperature of 16.2° C., is the selected solvent, the mold temperature can be reduced to as low as −40° C., depending on the size and shape of the injection port and geometry of the prosthesis. Preferably, the mold temperature is reduced to between 25° C. to 50° C. below the freezing temperature of the solvent.

During the solidification step, the injection pressure is preferably maintained on the mold cavity until solidification is complete to compensate for volume contraction of the solvent during solidification. Significant contraction of the solvent during solidification can result in the formation of shrinkage voids in the polymer structure and can reduce tolerances in the prosthesis. Additionally, by maintaining the injection pressure during solidification, the size of the mold cavity can be equal, or substantially equal to, the size of the desired prosthesis without concern for volume shrinkage during the solidification step.

Moreover, additional polymer solution can be injected into the mold fill voids created as a result of volume contraction during solidification. Since the part solidifies from the colder mold surface toward the warmer polymer, voids can be created in the center of the part. Preferably, the sprue area, i.e., the injection port, freezes last so that a continuous flow of polymer solution can be maintained into the thickest area of the prosthesis.

To further compensate for the effects of volume contraction during solidification, a solvent having a less than 10% volume change during solidification can be used.

After solidification, the prosthesis is demolded and dried by sublimation, block 506 of FIG. 5. Sublimation preferably occurs at a pressure lower than the vapor pressure of the solvent, at a temperature below the melting point of the solvent, and without the formation of a continuous liquid phase. The resultant prosthesis can be further dried using techniques such as critical point $CO_2$ drying.

A drug or drugs can be provided within the polymer prosthesis by adding the drug or drugs to the polymer solution prior to injection into the mold if the drug is soluble in the selected solvent. This will result in the drug being dispersed throughout the polymer structure of the prosthesis. In the alternative, an emulsion of the drug and a drug solvent can added to the polymer solution prior to injection resulting in the drug being retained in the pores of the dried polymer structure of the prosthesis after sublimation.

A prosthesis constructed from the injection molding process of the present invention can be used in tissue engineering and regeneration of a wide range of tissue types, including structural tissues, such as bone, muscle, or cartilage, and specialized tissues such as organ tissue, including brain and liver tissue, and breast tissue. The polymer foam-like structure of the prosthesis can provide a scaffold for the adherence of cells and/or a depot for growth promoting factors while concomitantly providing a porosity allowing for the diffusion of nutrients and gas exchange. In particular, the polymer foam-like structure of the prosthesis is suitable for either the seeding of cells in vitro to create new tissue constructs, such as the external ear, the trachea, bone, cartilage, or multi-component joints, or as a scaffold for the in-growth of regenerating tissue in vivo, such as nerve, mucosal lined surfaces, blood vessels, lymphatic vessels, liver, pancreas, kidney, intestine, parathyroid, thyroid, heart muscle, smooth muscle, skeletal muscle, and epithelial layers, including skin. The polymer structure can also serve as a local drug delivery device to deliver: inserted DNA encoding a protein that cells are deficient in, angiogenic factors, immunomodulators, molecules secreted by pancreatic cells, blood coagulation factors, factors stimulating differentiation, biologically active molecules stimulating lymphatic network, nerve or blood vessel ingrowth.

The injection molding process of the present invention provides significant advantages over alternative process for manufacturing prostheses because the exposure to the harsh solvents is minimized or eliminated and there is no exposure to high temperatures during the process, both of which can result in the denaturing of proteins. In addition, growth factors and drugs can be incorporated into the structure by addition to the polymer solution prior to injection.

Figure 4:
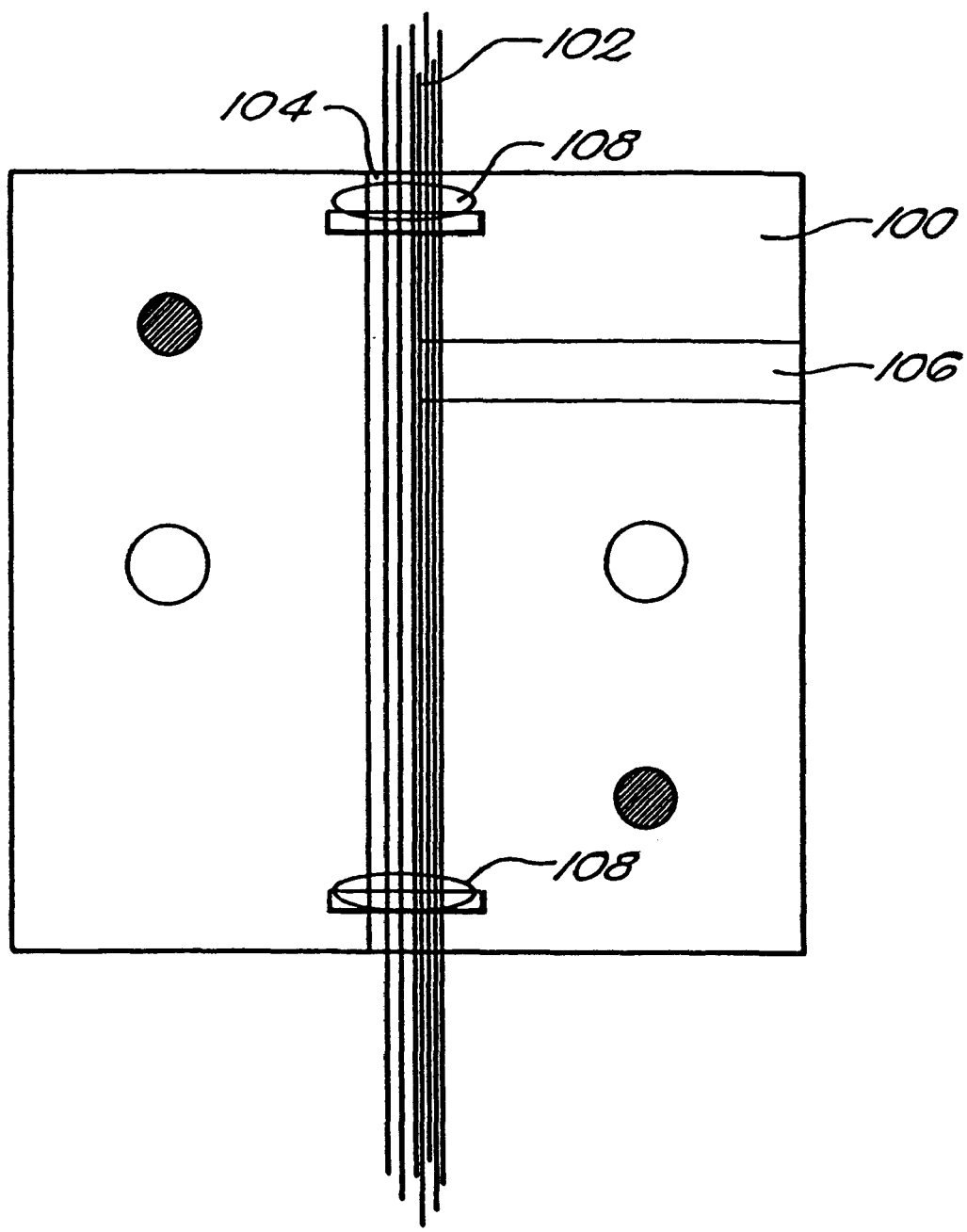
FIG. 4 is a top elevational schematic view of a mold suitable for use in constructing the nerve guidance channel of the present invention.

The nerve guidance channel 10 of the present invention can be manufactured using the injection molding process of the present invention. Referring to FIG. 4, a polymer solution, preferably a biodegradable polymer as discuss above, and a solvent, preferably acetic acid, is injected through injection port 106 into mold 100 under low pressure to form the polymeric body 12 of the nerve guidance channel 12. The mold 100 includes a plurality of wires 102 for forming the plurality of internal lumens within the body. The internal diameter of each of the lumens 20 can be controlled within a high tolerance using wires of varying outer diameters. The wires 102 are supported by two screen disks 108 within a cylindrical cavity 104 formed in the mold 100. The polymer solution is solidified by freezing. After solidification, the polymer solution is dried by sublimation to form a plurality pores within the body.

The concentration of the solvent within the polymer solution, the rate of solidification, the polymer solution injection temperature, and the mold temperature can be varied to control the porosity of the polymeric body of the nerve guidance channel. A drug can also be dispersed throughout the solution so that it will be released into the lumens of the nerve guidance chaimel over time.

The nerve guidance channel 10 of the present invention is used to span the gap between proximal and distal nerve stumps. The proximal and distal nerve stumps are each connected to an end 14, 16 of the body 12. The connections can be made by suturing each of ends of the 14, 16 of the body 12 to a respective one of the proximal nerve stump and the distal nerve stump.

Alternatively, an intermediate cylindrical tube, such as suture collar 80, can be sutured to each one of the proximal and distal nerve stumps for receiving a respective one of the ends 14, 16 of the body 12. Each of the intermediate cylindrical tubes 80 includes a single lumen having an inner diameter greater than the outer diameter of the body 12. Preferably, the length of each of the intermediate cylindrical tubes is shorter than the length of the length of the body 12. Once each intermediate cylindrical tube 80 is sutured to a nerve stump, each end 14, 16 is inserted into one the intermediate cylindrical tubes to thereby connect the body 12 to each of the nerve stumps.

A further alternative means of connecting the nerve guidance channel 10 to each of the proximal and distal nerve stumps by wrapping the nerve guidance channel in a collagen sheath. The ends of the collagen sheath, which extend beyond the ends 14, 16 of the body 12, are suitable for suturing to the nerve stumps.

The nerve guidance channel and method of the present invention are not limited solely to the repair of injured or severed peripheral nerves. The guidance channel can also can be used to promote nerve regeneration in the spinal cord as well as other areas of the central nervous system such as the optic nerve.

EXAMPLE I

A. Polymer Preparation

Conduits composed of a high molecular weight copolymer of lactic and glycolic acids (PLGA) (MW 130,000) were constructed according to the injection molding method of the present invention. PLGA was selected because it is known to be very well tolerated in vivo and has a degradation time that can be controlled by altering the ratio of the two monomers. The polymer is broken down by simple hydrolysis and the resultant products can be removed by the Kreb's cycle. In addition, PLGA has proven effective as a drug delivery vehicle.

Polylactide-co-glycolide (PLGA) in an 85:15 monomer ratio was purchased from Birmingham Polymers (Birmingham Ala.). A 10% solution (wt/wt) was prepared in reagent grade 99.99% glacial acetic acid (Aldrich, St. Louis Mo.) (Freezing Temperature $(T_f)$=16.2° C.). The solution was drawn into a glass syringe for injection molding in accordance with the injection molding method of the present invention. A stainless steel metal mold was fashioned to contain a cylindrical chamber. The mold was cooled in dry ice to below the $T_f$ of the PLGA/acetic acid solution. The solution was then injected into the cooled mold under low pressure by means of an injection port, where it was allowed to freeze rapidly. The mold was then opened in a clamshell fashion, and the frozen cylinder demolded. Subsequently, freeze-drying was undertaken at a vacuum pressure of 30–60 mtorr. Following drying, the processed polymer foams were stored in a dessicator under low vacuum for characterization and use.

B. Introduction of Lumenal Architecture

For the creation of channels or lumens within the polymer cylinders, a wire insert was prepared for the metal mold. Stainless steel wire, type 316V straightened (Small Parts Inc., Miami Lakes, Fla.) was cut into 14 cm lengths. Under 30× magnification, each wire was passed through two layers of stainless steel wire cloth, each pre-cut into ¼" round discs. The discs were then separated by 4.5 cm, so that each would sit in a slot at either end of the mold. Before the injection step, the mold was loaded with the wire insert, and the insert was secured at either end by means of a clamp. When utilizing wires of less than 300 $\mu$m OD, tension was introduced to pull the wires tautly with a simple spring at one end of the device.

Figure 6A:
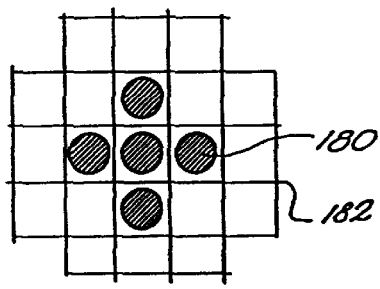
FIGS. 6A–C are side elevational, schematic views of a wire insert of the mold of the present invention, illustrating exemplary wire configurations.
Figure 6B:
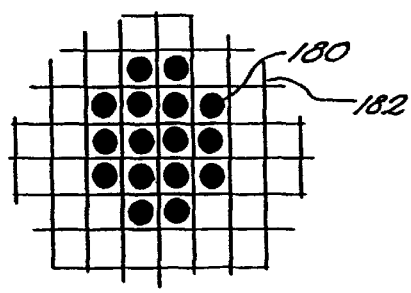
Figure 6C:
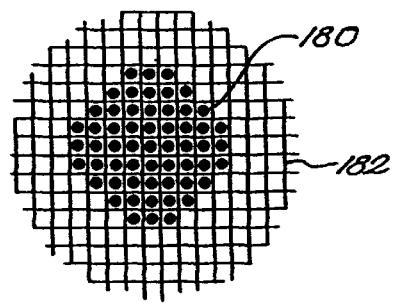

The wires had diameters of 60 to 500 microns, depending on the number and diameter of channels or lumens desired. The wires were positioned in different configurations through the wire cloth discs, so that different lumenal compositions were obtained. FIGS. 6A–B illustrate exemplary configurations of wires 180 threaded through wire cloth discs 182. FIG. 6A illustrates a 5 channel wire insert, FIG. 6B a 16 channel wire insert, and FIG. 6C a 57 channel wire insert.

C. Dynamic Seedino of Schwann Cells

Schwann cells were isolated from neonatal Fisher rats and were expanded for up to 12 weeks in culture, then either used or frozen for later use. The cell seeding was carried out in three stages. First, the conduits were pre-wet with physiologic saline, as follows. The conduits were placed inside a segment of silicone tubing and secured with a fitting. 50% EtOH was pumped through the polymer cylinder at a rate of 4 mL/min for 30 seconds and then was flushed out by flowing physiologic saline through the cylinder at 2 mL/min for the ensuing 12 hours. Second, the conduit was laminin coated by circulating a solution of 10 $\mu$g/mL laminin through the conduit for four hours.

Figure 7:
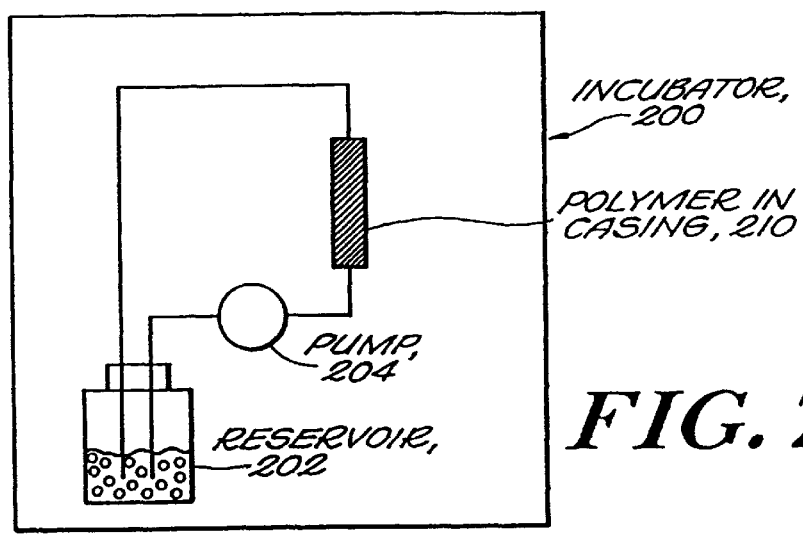
FIG. 7 is a schematic of a closed-loop bioreactor system for Schwann cell seeding according to the teachings of the present invention.

The conduit, in the silicone tubing, was then moved to a pump bioreactor inside an incubator (5% $CO_2$, 37° C.). FIG. 7 illustrates an exemplary closed-loop bioreactor system including incubator 200 and a pump 204 and reservoir 202 housed in the incubator and connected by suitable tubing. A suspension of Schwann cells ($5*10^5$/mL) was then pumped from the reservoir 202 through the laminin coated conduit 210 at a rate of 1 mL/min for four hours. Qualitative assessments of Schwann cell adherence were made by a MTT assay in which a solution of MTT was infused in the closed loop system, and after four hours the polymer conduits were inspected grossly for the presence of a dark purple tetrazoleum product produced by live cells only.

D. Results

Figure 8A:
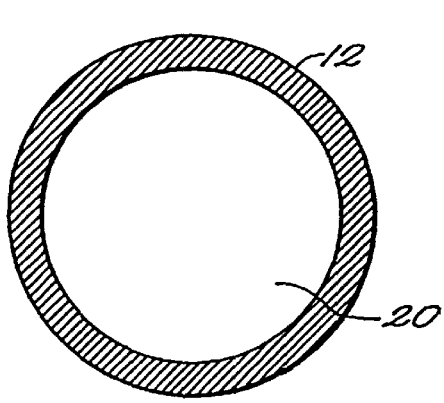
FIGS. 8A–8D are schematic views in cross-section of the nerve guidance channel of the present invention, illustrating exemplary lumen configurations.
Figure 8B:
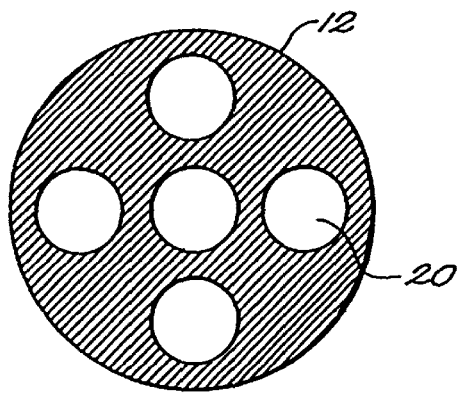
Figure 8C:
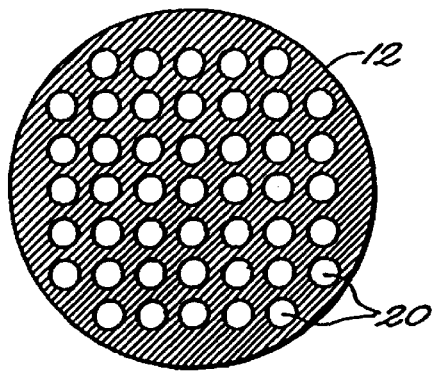
Figure 8D:
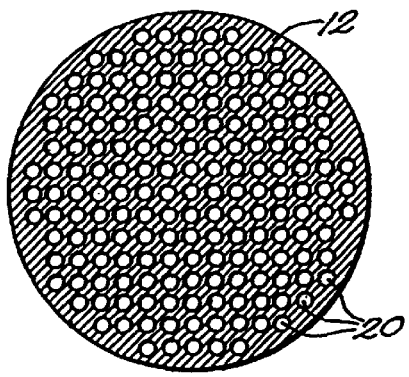

Conduits containing five (5) to eighty (80) lumens were created. Internal diameters of these channels ranged from 60 to 500 microns. The outer diameter of each conduit was 2.3 mm. The conduits were semi-rigid, but pliable and able to be manipulated into gentle curves to bridge nerve gaps. FIGS. 8A–8D illustrates schematically the cross-section of polymer conduits of various configurations after solvent removal. FIG. 8A illustrates a single lumen conduit, FIG. 8B illustrates a 5 lumen conduit, FIG. 8C illustrates a 45 lumen conduit, and FIG. 8D illustrates a 183 lumen conduit.

Figure 9A:
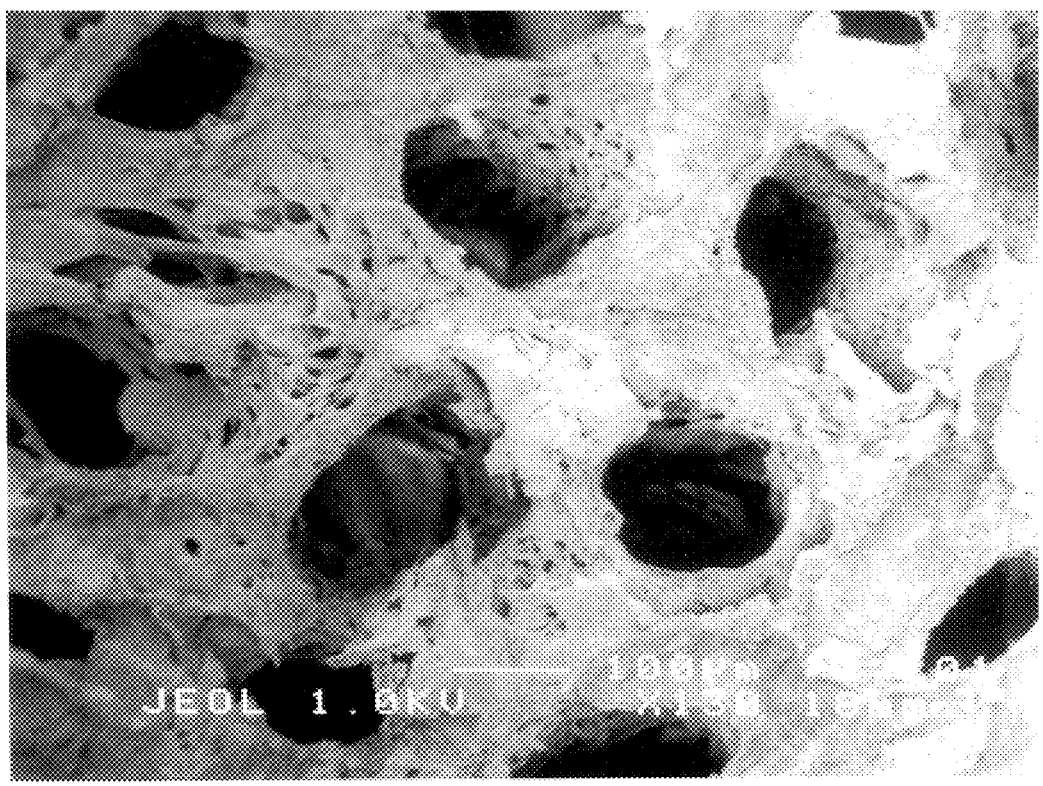
FIG. 9A is an electron micrograph of a cross-section of a 45-lumen nerve guidance channel at 130× magnification.
Figure 9B:
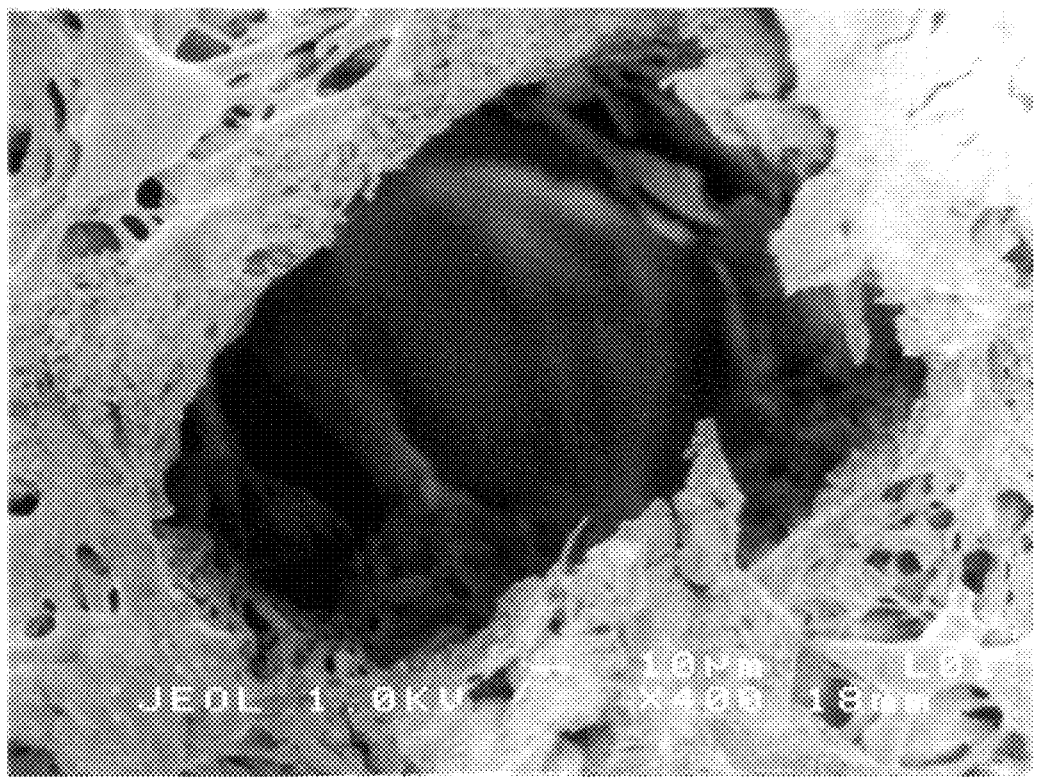
FIG. 9B is an electron micrograph of a cross-section of a 45-lumen nerve guidance channel at 370× magnification.

Electron microscopy revealed the expected network of pores. For example, FIG. 9A is an electron micrograph of a cross-section of a 45 lumen conduit at 130× magnification in which several lumens are visible. FIG. 9B is an electron micrograph of the 45 lumen conduit at 370× magnification in which a single lumen is visible. A comparison of the final weights of the processed foams indicated approximately 90% pore volume, as expected from the sublimation of acetic acid.

Following the dynamic seeding of Schwann cells as described, the presence of Schwann cells aligning the channels was verified histologically, using toluidine blue staining of longitudinal sections of the conduits.

The inventors have thus demonstrated that a synthetic conduit having a multi-lumen architecture can be produced using injection molding techniques and have also demonstrated the feasibility of introducing Schwann cells into the lumens in vitro. The specific advantages of this synthetic conduit are that the lumenal architecture can be specifically designed and controlled and that the polymer can be tailor made, offering far greater control over the direction of groups of regenerating fibers than that seen with autogenous materials.

The use of PLGA has several advantages. Because PLGA is 100% biodegradable, the regenerated nerve will not be encased in a foreign material. Entubulation with nonbiodegradable materials can lead to compression syndromes over time. Additionally, PLGA is an effective drug delivery vehicle, slowly releasing drugs or other substances over a protracted period. This property can be exploited for the purposes of differential regeneration of distinct neural fiber types.

EXAMPLE 2

A. In Vivo Regeneration Studies

In vivo regeneration studies were carried out in which Schwann cell laden 5-lumen polymer conduits (individual lumen ID 500 $\mu$m, total conduit OD 2.3 mm) were implanted across a 7 mm gap in the rat sciatic nerve (n=4), and midgraft axonal regeneration compared with autografts (n=6). The 5-lumen polymer conduits were constructed using the injection molding process described above in connection with Example 1 and were then coated with laminin and seeded with Schwann cells.

10 Fisher rats underwent microsurgical removal of a section of the left sciatic nerve, followed by conduit or autograft repair. After induction using inhalational methoxyfluorane anesthesia, animals were shaved and prepped in a sterile fashion. An incision was made over the left hind limb, and the gluteal musculature was divided to expose the sciatic nerve. For the conduit repairs, the nerve was sharply transected, allowed to contract, and sharply transected again to leave a 7 mm gap between cut ends. For autografts, a 7 mm section of the nerve was marked, sharply transected at both ends, and rotated so that the distal graft met the proximal stump and the proximal graft met the distal stump. The conduits or the autografts were secured into place using 2–3 10–0 nylon sutures at both ends, and the incision closed in layers. Animals were allowed to recuperate, and were given food and water ad libitum. Animal Care and Use Committee guidelines were followed. Autotomy was prevented or minimized by weekly treatment with Bitter Apple taste deterrent (Grannick's, Greenwich, Conn.) to the left foot.

After a period of six weeks, animals were sacrificed via methoxyfluorane overdose, and their sciatic nerves harvested. The nerves were fixed in 2.5% glutaraldehyde, postfixed in osmium tetroxide, and epoxy embedded for histologic analysis. Sections 1 $\mu$m in thickness were toluidine blue stained, and histomorphometric analysis of the neural regenerate present in the midconduit region was performed.

B. Results

Figure 10:
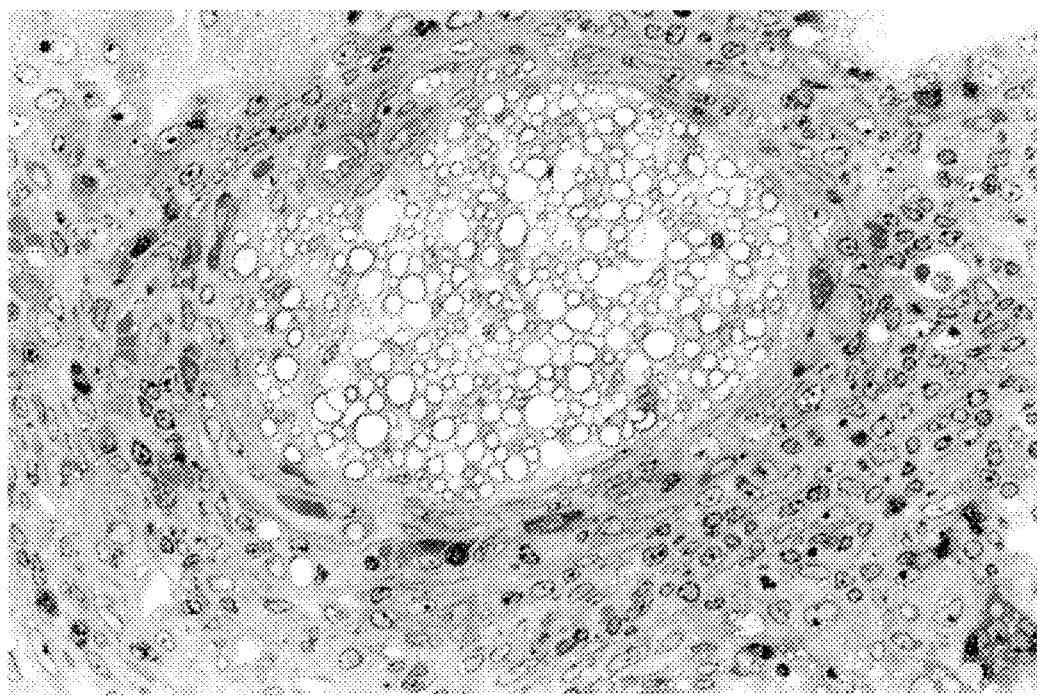
FIG. 10 is an electron micrograph of a histological cross-section of a toluidine blue stained 5-lumen nerve guidance channel at 200× magnification, illustrating nerve regenerate in a lumen of the nerve guidance channel.

Upon harvest, all polymer conduits were found to be intact, with no anastomotic disruptions or fractures along the length of the conduit. Histologic examination of the toluidine blue stained midconduit sections revealed the presence of a neural regenerate in each of the longitudinally aligned channels in all experimental animals (n=4). FIG. 10 is an electron micrograph of a histological cross section of toluidine blue stained conduit illustrating neural regenerate in a lumen of the conduit. All autografted animals demonstrated regeneration consistent with levels in the literature for similar gap lengths and survival time. Results of histomorphometric analysis are shown in table 1.

TABLE 1

Histomorphometric analysis of 5-lumen conduits and autografts

| TYPE OF REPAIR | MEAN NEURAL FIBER WIDTH ($\mu$m) | NEURAL FIBER DENSITY (fibers/$\mu$m$^2$) | TOTAL FIBER NUMBER | % NEURAL TISSUE |
|---|---|---|---|---|
| PLGA CONDUIT | 3.73 ± 0.51 | 18179 ± 3306 | 1226 ± 319 | 26.3 ± 10.1 |
| AUTO-GRAFT | 2.54 ± 0.24 | 28747 ± 6781 | 12189 ± 4925 | 23.8 ± 3.6 |

At six weeks, the percentage of neural tissue per cross sectional open area through the polymer conduits (26.3%) was slightly better than those through autografts (23.8%), though the difference was not statistically significant. The mean axon diameter was 3.7 $\mu$m, significantly greater than that through control autografts, having a mean diameter of only 2.5 $\mu$m.

In this pilot group of animals, the inventors have shown that regeneration is not only possible through the polymer conduit, but may provide an environment more favorable to regeneration than that provided by autografts. The fact that the average fiber diameter found in the polymer conduits was significantly higher than that in the autografts suggests that the regenerative environment in the polymer prosthesis may favor regeneration of myelinated ("fast") motor fibers. This has broad implications in peripheral nerve surgical repair, as optimal motor function is the ultimate clinical goal.

The total fiber number through the synthetic conduits remained quite low in comparison with that seen through the autografts. This is simply because the 5-lumen prostheses had a relatively low open cross-sectional conduit area (20%). Given the quality of the neural regenerate in each channel however, the provision of additional channels within the conduits will lead to a higher overall fiber number.

It is to be understood that the present invention is not limited to the embodiments described above, but encompasses any and all embodiments within the scope of the following claims:

What is claimed is:

1. A method for manufacturing a polymeric prosthesis, the method comprising the steps of:

preparing a polymer solution comprising a polymer and a solvent, injecting the polymer solution into the mold cavity of a mold at an injection pressure to form a body of a polymeric prosthesis, the mold including a plurality of wires, which form a plurality of lumens within the body;

solidifying the polymer solution to form the polymeric prosthesis by freezing the polymer solution in the mold; and drying the polymeric prosthesis by sublimation.

2. The method according to claim 1, wherein the solvent is selected from the group consisting of aromatics and chlorinated hydrocarbons.

3. The method according to claim 1, wherein the solvent is acetic acid.

4. The method according to claim 1, wherein the polymer is polylactic acid (PLA).

5. The method according to claim 1, wherein the polymer is polylactide co-glycolide (PLGA).

6. The method according to claim 1, wherein the step of solidification further comprises decreasing the temperature of the polymer solution in the mold to a temperature below the freezing temperature of the polymer solution.

7. The method according to claim 6, wherein the temperature of the polymer solution in the mold is decreased to approximately between 25° C. to 50° C. below the freezing temperature of the polymer solution.

8. The method according to claim 1, further comprising the step of maintaining the injection pressure in the mold cavity during the step of solidifying the polymer solution.

9. The method according to claim 1, wherein the step of drying the prosthesis occurs at a pressure below the vapor pressure of the solvent.

10. The method according to claim 1, wherein the step of drying the prosthesis occurs at a temperature below the melting point of the solvent.

11. The method according to claim 1, wherein the step of drying occurs without the formation of a continuous liquid phase.

12. The method according to claim 1, further comprising the step of providing a drug within the polymer prosthesis.

13. The method according to claim 12, wherein the step of providing a drug comprises the step of introducing the drug to the polymer solution prior to injection of the polymer solution into the mold cavity.

14. The method according to claim 1, wherein the polymer is polyglycolic acid (PGA).

* * * * *

UNITED STATES PATENT AND TRADEMARK OFFICE
CERTIFICATE OF CORRECTION

PATENT NO.    : 6,214,021 B1
DATED         : April 10, 2001
INVENTOR(S)   : Theresa A. Hadlock and Cathryn Sundback Page 1 of 1

It is certified that error appears in the above-identified patent and that said Letters Patent is hereby corrected as shown below:

<u>Column 3,</u>
Line 53, "between 5 and 500" should read -- between 5 and 5000 --

<u>Column 5,</u>
Line 35, "By varyino" should read -- By varying --

<u>Column 8,</u>
Line 5, "guidance chaimel over time" should read -- guidance channel over time --

Signed and Sealed this

Twenty-fifth Day of December, 2001

*Attest:*

JAMES E. ROGAN
*Attesting Officer*     *Director of the United States Patent and Trademark Office*